United States Patent [19]
Whitman

[11] Patent Number: 6,026,176
[45] Date of Patent: Feb. 15, 2000

[54] MACHINE VISION METHODS AND ARTICLES OF MANUFACTURE FOR BALL GRID ARRAY INSPECTION

[75] Inventor: Steven M. Whitman, Danville, N.H.

[73] Assignee: Cognex Corporation, Natick, Mass.

[21] Appl. No.: 08/521,959

[22] Filed: Aug. 31, 1995

Related U.S. Application Data

[60] Provisional application No. 60/001,430, Jul. 25, 1995.

[51] Int. Cl.⁷ .................................................... G06K 9/00
[52] U.S. Cl. ........................ 382/146; 382/147; 382/150; 382/151
[58] Field of Search .................................. 382/141, 145, 382/147, 149–152, 144, 148; 348/86–87, 94–95; 364/557, 558; 702/155, 199

[56] References Cited

U.S. PATENT DOCUMENTS

| | | |
|---|---|---|
| 3,816,722 | 6/1974 | Sakoe et al. . |
| 3,936,800 | 2/1976 | Ejiri et al. ................................. 382/18 |
| 3,967,100 | 6/1976 | Shimomura . |
| 3,968,475 | 7/1976 | McMahon ................................. 382/18 |
| 3,978,326 | 8/1976 | Shimomura . |
| 4,011,403 | 3/1977 | Epstein et al. . |
| 4,115,702 | 9/1978 | Nopper ................................. 382/48 |
| 4,183,013 | 1/1980 | Agrawala et al. . |
| 4,200,861 | 4/1980 | Hubach et al. ........................... 382/34 |
| 4,254,400 | 3/1981 | Yoda et al. ............................... 382/18 |
| 4,300,164 | 11/1981 | Sacks . |
| 4,385,322 | 5/1983 | Hubach et al. . |
| 4,441,124 | 4/1984 | Heebner et al. . |
| 4,441,206 | 4/1984 | Kuniyoshi et al. .......................... 382/8 |
| 4,534,813 | 8/1985 | Williamson et al. . |
| 4,541,116 | 9/1985 | Lougheed . |
| 4,570,180 | 2/1986 | Baier et al. . |

(List continued on next page.)

FOREIGN PATENT DOCUMENTS

| | | |
|---|---|---|
| 0 527 632 A2 | 2/1993 | European Pat. Off. . |
| WO 95/122137 | 8/1995 | WIPO . |
| WO 95/21376 | 8/1995 | WIPO . |
| WO 97/21189 | 6/1997 | WIPO . |
| WO 97/22858 | 6/1997 | WIPO . |
| WO 97/24692 | 7/1997 | WIPO . |
| WO 97/24693 | 7/1997 | WIPO . |

OTHER PUBLICATIONS

Grimson, Member, Ieee and Huttenlocher, *On the Sensitivity of the Hough Transform for Object Recognition*, 1990, p. 255.

Grimson, Member, Ieee and Huttenlocher, *On the Sensitivity of the Hough Transform for Object Recognition*, 1990, p. 123.

Grimson, W. Eric L. and Huttenlocher, Daniel P., "On the Sensitivity of the Hough Transform for Object Recognition", May 1990, IEEE Transactions on Pattern Analysis and Machine Intelligence, vol. 12, No. 3.

(List continued on next page.)

*Primary Examiner*—Bhavesh Mehta
*Attorney, Agent, or Firm*—David J. Powsner

[57] ABSTRACT

A method of inspecting an image to locate a ball grid array surface-mounted device includes the steps of inspecting the image to find its surface features and to determine their locations (referred to herein as their "observed" locations); comparing expected locations of those features with the observed locations to identify missing surface features; reinspecting the image in the vicinity of apparently missing surface features to verify if the feature is really missing or to find those features and to determine their "observed" locations; and determining, from the observed locations of the surface features, the position and/or angle of the ball grid array surface-mounted device. The invention can be used to determine the position and/or angle of ball grid array surface-mounted devices with surface features in any of many array configurations, e.g., a regular lattice, a checker board lattice, a reverse checker board lattice, a regular lattice with a holes, and a custom lattice.

5 Claims, 6 Drawing Sheets

U.S. PATENT DOCUMENTS

| | | |
|---|---|---|
| 4,577,344 | 3/1986 | Warren et al. . |
| 4,581,762 | 4/1986 | Lapidus et al. . |
| 4,606,065 | 8/1986 | Beg et al. . |
| 4,617,619 | 10/1986 | Gehly . |
| 4,630,306 | 12/1986 | West et al. ............................ 382/21 |
| 4,688,088 | 8/1987 | Hamazaki et al. ................... 358/101 |
| 4,706,168 | 11/1987 | Weisner . |
| 4,728,195 | 3/1988 | Silver . |
| 4,730,260 | 3/1988 | Mori et al. . |
| 4,731,858 | 3/1988 | Grasmueller et al. . |
| 4,736,437 | 4/1988 | Sacks et al. ............................ 382/34 |
| 4,742,551 | 5/1988 | Deering . |
| 4,764,870 | 8/1988 | Haskin . |
| 4,771,469 | 9/1988 | Wittenburg . |
| 4,783,826 | 11/1988 | Koso et al. ............................. 382/8 |
| 4,783,828 | 11/1988 | Sadjadi .................................. 382/170 |
| 4,783,829 | 11/1988 | Miyakawa et al. . |
| 4,831,580 | 5/1989 | Yamada . |
| 4,860,374 | 8/1989 | Murakami et al. .................... 382/48 |
| 4,860,375 | 8/1989 | McCubbrey et al. . |
| 4,876,457 | 10/1989 | Bose . |
| 4,876,728 | 10/1989 | Roth ....................................... 382/8 |
| 4,903,218 | 2/1990 | Longo et al. . |
| 4,907,169 | 3/1990 | Lovoi ..................................... 382/8 |
| 4,914,553 | 4/1990 | Hamada et al. . |
| 4,922,543 | 5/1990 | Ahlbom et al. ...................... 382/48 |
| 4,926,492 | 5/1990 | Tanaka et al. ........................ 382/18 |
| 4,932,065 | 6/1990 | Feldgajer . |
| 4,953,224 | 8/1990 | Ichinose et al. . |
| 4,955,062 | 9/1990 | Terui ..................................... 382/8 |
| 4,959,898 | 10/1990 | Landman et al. .................... 29/705 |
| 4,962,423 | 10/1990 | Yamada et al. ...................... 358/101 |
| 4,972,359 | 11/1990 | Silver et al. ......................... 364/728.5 |
| 4,982,438 | 1/1991 | Usami et al. . |
| 5,012,402 | 4/1991 | Akiyama . |
| 5,046,190 | 9/1991 | Daniel et al. . |
| 5,054,096 | 10/1991 | Beizer . |
| 5,060,276 | 10/1991 | Morris et al. . |
| 5,063,608 | 11/1991 | Siegel . |
| 5,073,958 | 12/1991 | Imme ..................................... 382/22 |
| 5,081,656 | 1/1992 | Baker et al. ........................... 382/8 |
| 5,081,689 | 1/1992 | Meyer et al. . |
| 5,086,478 | 2/1992 | Kelly-Mahaffey et al. ............ 382/8 |
| 5,090,576 | 2/1992 | Menten . |
| 5,091,861 | 2/1992 | Geller et al. .......................... 364/474.34 |
| 5,091,968 | 2/1992 | Higgins et al. . |
| 5,093,867 | 3/1992 | Hori et al. . |
| 5,113,565 | 5/1992 | Cipolla et al. ........................ 382/8 |
| 5,115,309 | 5/1992 | Hang . |
| 5,119,435 | 6/1992 | Berkin . |
| 5,124,622 | 6/1992 | Kawamura et al. . |
| 5,133,022 | 7/1992 | Weideman ............................ 382/18 |
| 5,134,575 | 7/1992 | Takagi .................................. 364/559 |
| 5,143,436 | 9/1992 | Baylor et al. . |
| 5,145,432 | 9/1992 | Midland et al. . |
| 5,151,951 | 9/1992 | Ueda et al. . |
| 5,153,925 | 10/1992 | Tanioka et al. . |
| 5,159,281 | 10/1992 | Hedstrom et al. . |
| 5,159,645 | 10/1992 | Kumagai . |
| 5,164,994 | 11/1992 | Bushroe ................................. 382/150 |
| 5,168,269 | 12/1992 | Harlan . |
| 5,185,855 | 2/1993 | Kato et al. . |
| 5,189,712 | 2/1993 | Kajiwara et al. . |
| 5,206,820 | 4/1993 | Ammann et al. ..................... 364/559 |
| 5,216,503 | 6/1993 | Paik . |
| 5,225,940 | 7/1993 | Ishii et al. . |
| 5,230,027 | 7/1993 | Kikuchi . |
| 5,243,607 | 9/1993 | Masson et al. . |
| 5,253,306 | 10/1993 | Nishio . |
| 5,253,308 | 10/1993 | Johnson . |
| 5,265,173 | 11/1993 | Griffin et al. . |
| 5,271,068 | 12/1993 | Ueda et al. . |
| 5,287,449 | 2/1994 | Kojima . |
| 5,297,256 | 3/1994 | Wolstenholme et al. . |
| 5,299,269 | 3/1994 | Gaborski et al. . |
| 5,311,598 | 5/1994 | Bose et al. ............................ 382/149 |
| 5,315,388 | 5/1994 | Shen et al. . |
| 5,319,457 | 6/1994 | Nakahashi et al. . |
| 5,327,156 | 7/1994 | Masukane et al. . |
| 5,337,267 | 8/1994 | Colavin . |
| 5,363,507 | 11/1994 | Nakayama et al. . |
| 5,367,439 | 11/1994 | Mayer et al. . |
| 5,367,667 | 11/1994 | Wahlquist et al. . |
| 5,371,690 | 12/1994 | Engel et al. .......................... 364/570 |
| 5,388,197 | 2/1995 | Rayner . |
| 5,388,252 | 2/1995 | Dreste et al. . |
| 5,398,292 | 3/1995 | Aoyama . |
| 5,432,525 | 7/1995 | Maruo et al. . |
| 5,440,699 | 8/1995 | Farrand et al. . |
| 5,455,870 | 10/1995 | Sepai et al. . |
| 5,455,933 | 10/1995 | Schieve et al. . |
| 5,475,766 | 12/1995 | Tsuchiya et al. . |
| 5,477,138 | 12/1995 | Efjavic et al. . |
| 5,481,712 | 1/1996 | Silver et al. . |
| 5,485,570 | 1/1996 | Bushboom et al. . |
| 5,491,780 | 2/1996 | Fyles et al. . |
| 5,495,424 | 2/1996 | Tokura .................................. 364/507 |
| 5,495,537 | 2/1996 | Bedrosian et al. . |
| 5,519,840 | 5/1996 | Matias et al. . |
| 5,526,050 | 6/1996 | King et al. . |
| 5,532,739 | 7/1996 | Garakani et al. ..................... 382/150 |
| 5,544,256 | 8/1996 | Brecher et al. ....................... 382/149 |
| 5,550,763 | 8/1996 | Michael et al. ...................... 382/145 |
| 5,566,877 | 10/1996 | McCormack . |
| 5,568,563 | 10/1996 | Tanaka et al. . |
| 5,574,668 | 11/1996 | Beaty .................................... 364/558 |
| 5,574,801 | 11/1996 | Collet-Beillon ...................... 382/150 |
| 5,583,954 | 12/1996 | Garakani . |
| 5,586,058 | 12/1996 | Aloni et al. ........................... 382/148 |
| 5,592,562 | 1/1997 | Rooks ................................... 382/150 |
| 5,594,859 | 1/1997 | Palmer et al. . |
| 5,602,937 | 2/1997 | Bedrosian et al. . |
| 5,608,872 | 3/1997 | Schwartz et al. . |
| 5,640,199 | 6/1997 | Garakani et al. . |
| 5,640,200 | 6/1997 | Michael . |

OTHER PUBLICATIONS

Medina–Mora et al. (1981) An Incremental Programming Environment, IEEE Transactions on Software Eng. SE–7:472–482.

Teitelbaum et al. (19810 The Cornell Program Synthesizer: A Syntax–Directed Programming Environment, Communications of the ACM 24:563–573.

Newsletter from Acquity Imaging, Inc., "Remote Vision Support Package—The Phones Are Ringing!," 1 page.

PictureTel Corporation Product Brochure "Picturetel Live PCS 100(tm) Personal Visual Communications System," 3 pp. (1993).

PictureTel Corporation Product Brochure "PictureTel System 1000: Complete Videoconferencing for Cost Sensitive Applications," 4 pp. (1993).

PictureTel Corporation Product Brochure, "PictureTel System 4000(tm) A Family of Models to Fit Your Application from Offices to Boardrooms, Classrooms, and Auditoriums," 4 pp. (1993).

Symantec Corporation, "The Norton pcAnywhere User's Guide," Table of Contents 8 pp; Introduction of pcAnywhere Technology pp i–vii; Chapter 7—Sessions; pp. 191–240 (1991).

Bursky, Dave, "CMOS Four–Chip Set Process Images at 20–MHz Data Rates," Electronic Design, May 28, 1987, pp. 39–44.

Plessey Semiconductors, Preliminary Information, May 1986, Publication No. PS2067, May 1986, pp. 1–5.

NEC Electronics Inc., PD7281 Image Pipelined Processor, Product Information Brochure, pp. 2–169—2–211.

Horn, Berthold Klaus Paul. "Robot Vision", The Massachusetts Institute for Technology, 1986.

Rosenfeld, Azriel. "Computer Vision: Basic Principles," Proceedings of the IEEE. vol. 76, No. 8, Aug. 1988. pp. 863–868.

```
o o o o o      o . o . o      . o . o .      o o o o o
o o o o o      . o . o .      o . o . o      o o o o o
o o o o o      o . o . o      . o . o .      o o . o o
o o o o o      . o . o .      o . o . o      o o . o o
o o o o o      o . o . o      . o . o .      o o o o o
 Regular        Checker       R-Checker      Grid w/hole . o o o .      o o o o o
o o o o o      o o o . o
o o o o o      o o o o o
o o o o o      o . o o o
. o o o .      o o o o o Grids w/holes
```

(o - ball, . - intentionally missing ball(s))

Figure 3

```
.  X  X  X  X  X  X  X           X = Potenial ball site

X  O  O  O  O  O  O  X           O = Found ball site

X  O  O  O  *  O  X  X           * = Expected ball site

X  O  *  *  O  O  X  X           . = Attempted ball site

X  *  O  O  O  *  O  X           @ = Actual ball site

MACHINE VISION METHODS AND ARTICLES OF MANUFACTURE FOR BALL GRID ARRAY INSPECTION

REFERENCE TO RELATED APPLICATIONS

This application claims the benefit of the filing date of copending U.S. Provisional Application No. 60/001,430, filed Jul. 25, 1995, for IMPROVED MACHINE VISION METHODS AND ARTICLES OF MANUFACTURE FOR BALL GRID ARRAY INSPECTION (Attorney Docket No. 150448-006). The teachings of that provisional patent application, including the appendices filed therewith, are incorporated by reference herein.

RESERVATION OF COPYRIGHT

The disclosure of this patent document contains material which is subject to copyright and/or mask work protection. The owner thereof has no objection to facsimile reproduction by anyone of the patent document or the patent disclosure, as it appears in the U.S. Patent and Trademark Office patent file or records, but otherwise reserves all copyright and/or mask work rights whatsoever.

BACKGROUND OF THE INVENTION

The invention pertains to machine vision and, more particularly, to methods and articles of manufacture for inspecting ball grid array devices.

In automated assembly processes, such as those for assembling electronic circuit boards, it is important to determine the exact location of components prior to their placement for final assembly. For example, an assembly system must know the axial position and angular orientation of each component before placing its leads on appropriate solder pads of a printed circuit board.

Accuracy in positioning is ever more critical as the ratio of the size of the electronic components to the number of conductive leads increases. Such is the case with ball grid array (BGA) devices. These are small surface mounted devices containing tens or hundreds of conductive solder "bumps" arranged in regular patterns, e.g., rectangular arrays, "checker boards", et cetera. Because the bumps are so closely spaced, accurate placement and alignment with solder pads on the circuit board is imperative.

The art suggests a few approaches to determining the orientation of BGA devices. These approaches are primarily binary techniques based on "blob" analysis of the solder bump array images. A drawback of the approaches is that, due to their binary nature, they are highly susceptible to lighting conditions or device-to-device variations. Moreover, they require that correspondence steps be performed to remove extraneous features, or noise. Those correspondence steps are typically very time consuming. While some approaches have attempted to reduce that time by limiting the correspondence step to a small subset of the bumps, those approaches suffer reduced accuracy.

An object of this invention is to provide improved methods for machine vision analysis and, particularly, improved methods for inspection of ball grid array devices.

A more particular object of this invention is to provide improved methods for BGA device inspection that permit the placement and orientation of those components to be readily and accurately determined.

Yet still another object of the invention is to provide such methods that can execute quickly, and without consumption of excessive resources, on a wide range of machine vision analysis equipment.

Still yet another object of the invention is to provide articles of manufacture comprising a computer usable medium embodying program code for carrying out improved such methods.

SUMMARY OF THE INVENTION

The foregoing objects are attained by the invention which provides, in one aspect, a method of inspecting an image to locate a ball grid array surface-mounted device characterized by an array of similar surface features, e.g., solder bumps. The method includes the steps of inspecting the image to find its surface features and to determine their locations (referred to herein as their "observed" locations); comparing expected locations of those features with the observed locations to identify missing surface features; reinspecting the image in the vicinity of apparently missing surface features to verify if the feature is really missing or to find those features and to determine their "observed" locations; and determining, from the observed locations of the surface features, the position and/or angle of the ball grid array surface-mounted device.

The invention can be used to determine the position and/or angle of ball grid array surface-mounted devices with surface features in any of many array configurations, e.g., a regular lattice, a checker board lattice, a reverse checker board lattice, a regular lattice with a holes.

In further aspects, the invention calls for finding the convex hull (i.e., perimeter) and hull angle (i.e., angular orientation of the perimeter) of the observed surface features. From those, a grid of expected locations of the surface features can be generated. Each of the observed locations can be assigned to the closest vertex on the grid. A score is then generated based on the number of surface features assigned to each vertex and the distance between each such vertex and its assigned surface features.

In a related aspect of the invention, the position and/or angle of the ball grid array surface-mounted device can be determined by performing a rigid body fit of the observed locations of surface features to the grid of expected locations.

These and other aspects of the invention are evident in the drawings and in the description that follows.

BRIEF DESCRIPTION OF THE DRAWINGS

A more complete understanding of the invention may be attained by reference to the drawings, in which.

DETAILED DESCRIPTION OF THE ILLUSTRATED EMBODIMENT

Figure 1:
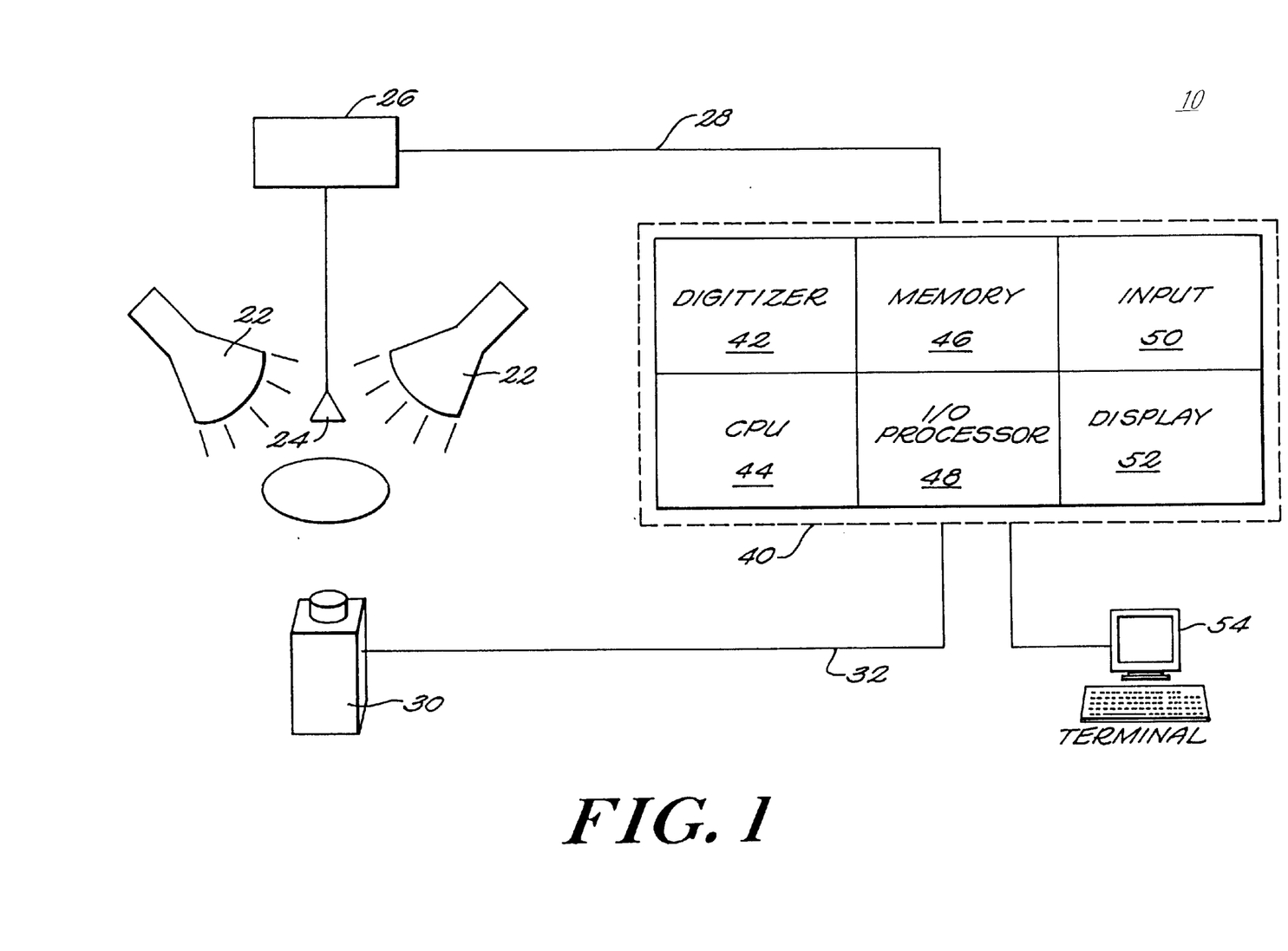
FIG. 1 is a diagrammatic representation of a machine vision system for determining the orientation of an object by image processing and analysis.

FIG. 1 is a diagrammatic representation of a machine vision system 10 for determining the orientation of an object by image processing and analysis. The system 10 includes a video camera 30 for generating a video signal 32 depicting the front of an object 20 being inspected. Lighting sources 22 provide illumination, e.g., that illuminates the object 20 from the front. A pickup device 24, such as a robotic gripper or suction nozzle, holds the object 20 during inspection. Actuator 26, such as a servo or robotic actuator, moves the pickup 24 and, thereby, the object 20.

The machine vision system 10 further includes an image analyzing system 40 for performing an automatic vision analysis of the object 20. The image analyzing system 40 determines characteristics of the object 20, such as position, boundary and orientation, based on processing and analyzing the video image signal 32 from the video camera 30.

In a preferred embodiment of the invention, image analyzer 40 represents a conventional digital data processing system having an image digitizer 42, memory 46, at least one CPU 44, and input/output processing elements 48 for interfacing the system 40 to peripheral input and output devices. The image analyzer may also include input devices 50, such as a keyboard or mouse, and output devices 52, such as a display monitor and printer as well as interface with one or more terminals 54.

Image analyzer 40 and its components 42–54 comprise any commercially available digital data processor, e.g., a personal computer or workstation, programmed for operation in accord with the teachings of this application. Preferred image analyzers 40 suitable for such programming are sold by the assignee hereof, Cognex Corporation. Those skilled in the art will appreciate that programming the analyzer 40 for operation in accord with the teachings of the invention includes storing in memory 46 (and, optionally, other computer readable storage media, such as magnetic diskettes or hard disks) a computer program that enables CPU 44 to carry out the methodology of FIG. 2.

BGA devices present several challenges to inspect with a machine vision system. Some of the problems faced when inspection a BGA include the large number of balls; the lack of contrast between ball and background; the irregular ball shapes; the degradation of ball image and reflectivity due to oxidation; the large BGA device size; the varied packing types and the need to necessity of inspecting quickly. The inspection methodology described herein overcomes these problems in a manner superior to that attained by the prior art.

Training/Inspection Overview

Device Training

Figure 3:
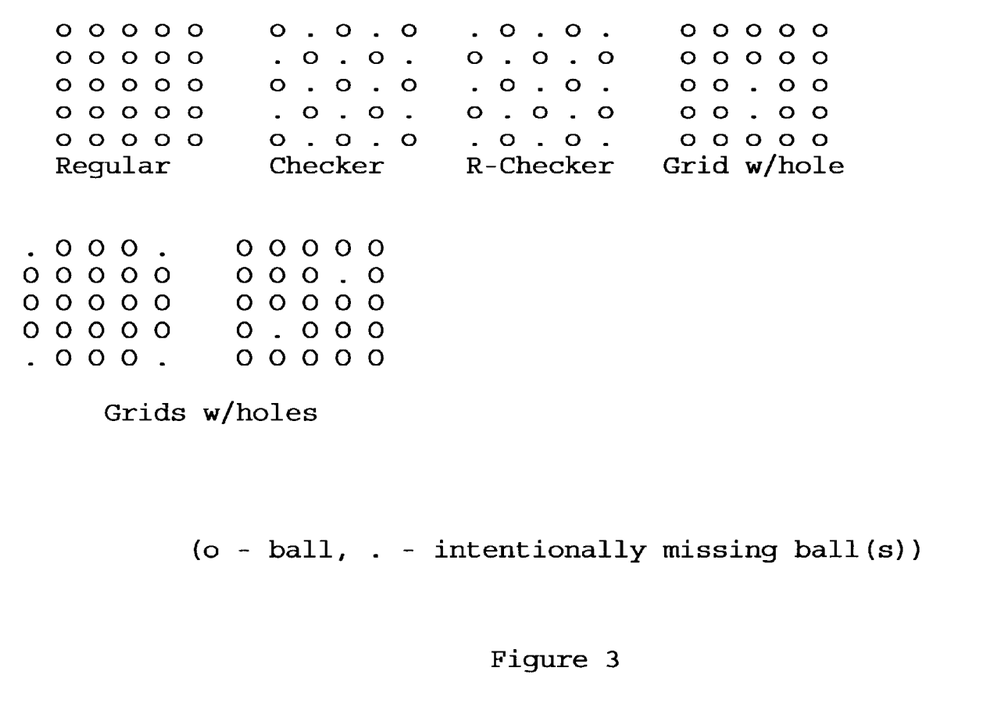
FIG. 3 depicts BGA device solder bump grid pattern styles amenable to inspection by the invention.

BGA devices come in a variety of packaging styles with several grid patterns. A device description allows a user to describe the geometrical layout of a BGA device. This description, which is used as input to the training phase is as follows:

Overall Size (Width, Height)
Number of ball rows
Number of ball columns
Grid pattern style (regular, checkerboard, reverse checkerboard and grid with a holes). See FIG. 3, which depicts a plurality of BGA device solder bump grid patterns amenable to inspection by the illustrated embodiment. These include a regular pattern in which the solder bumps form a regular rectilinear matrix, as shown. These also include checkerboard and reverse checkerboard patterns (labeled "Checker" and "R-Checker"in the drawings), in which every other solder bump of an otherwise regular rectilinear matrix is missing, as shown. These also include BGA grids with holes, in which occasional solder bumps are missing from an otherwise regular rectilinear matrix, as shown.
Grid spacing (pitch)
Ball size (diameter)
For grids with holes, the starting row, column and number of rows, columns of missing balls for each hole.

This device description describes the attributes of the BGA that are invariant for a given component (packaging style, substrate color, etc. may vary for a given component) and are used to perform the inspection.

The following two steps are performed to construct (or "train") a device inspection. These steps occur at some point in time prior to performing the inspection:

1) Using the device description, construct one or more locators. It is the locator that does the actual work to find the ball(s). Additional information (dependant on the locator) is also provided.

2) Using the device description and the locators, construct a device inspection.

Device Inspection

Figure 2A:
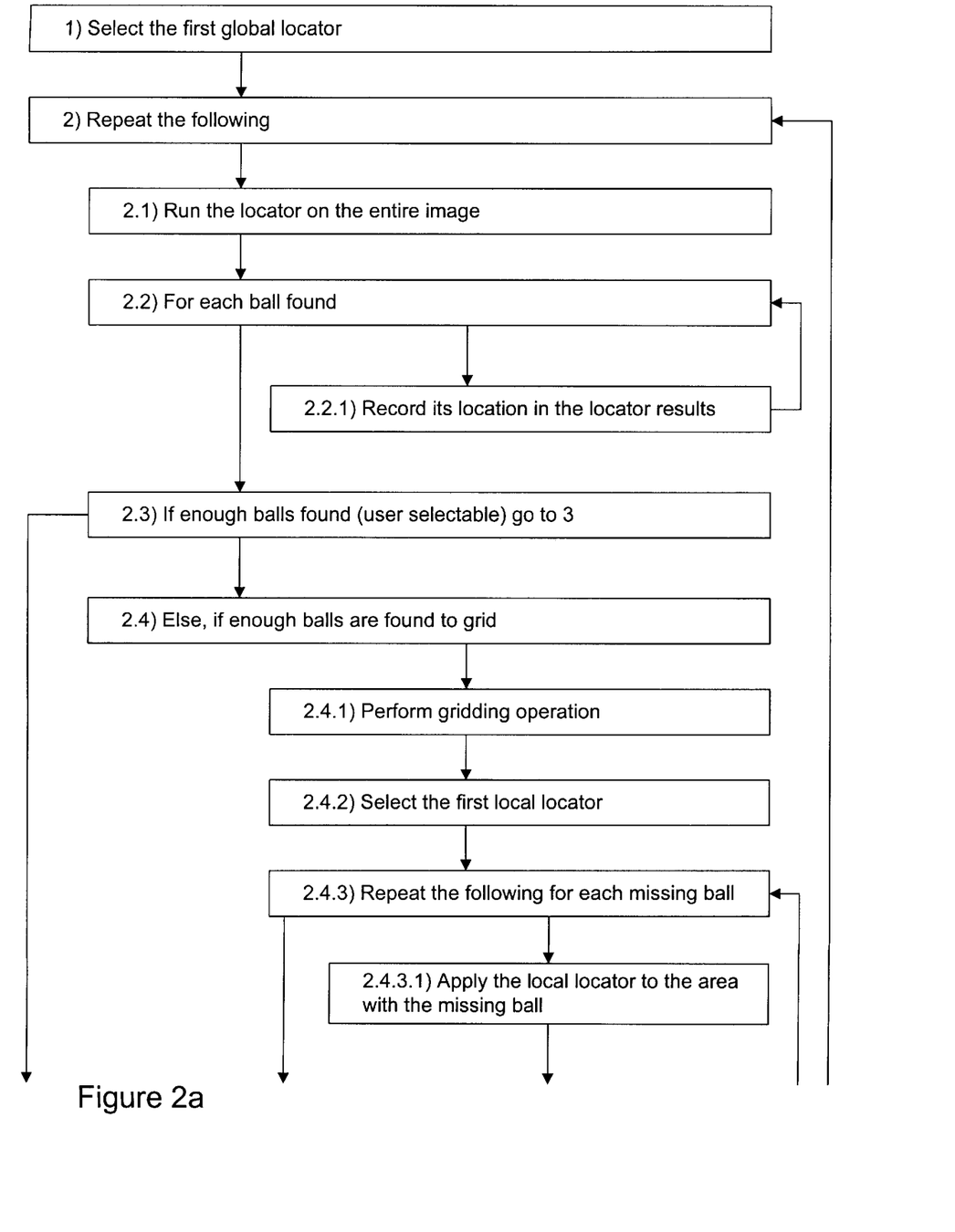
FIGS. 2A–2C depicts a method according to the invention for inspecting an image of a ball grid array surface-mounted device.
Figure 2B:
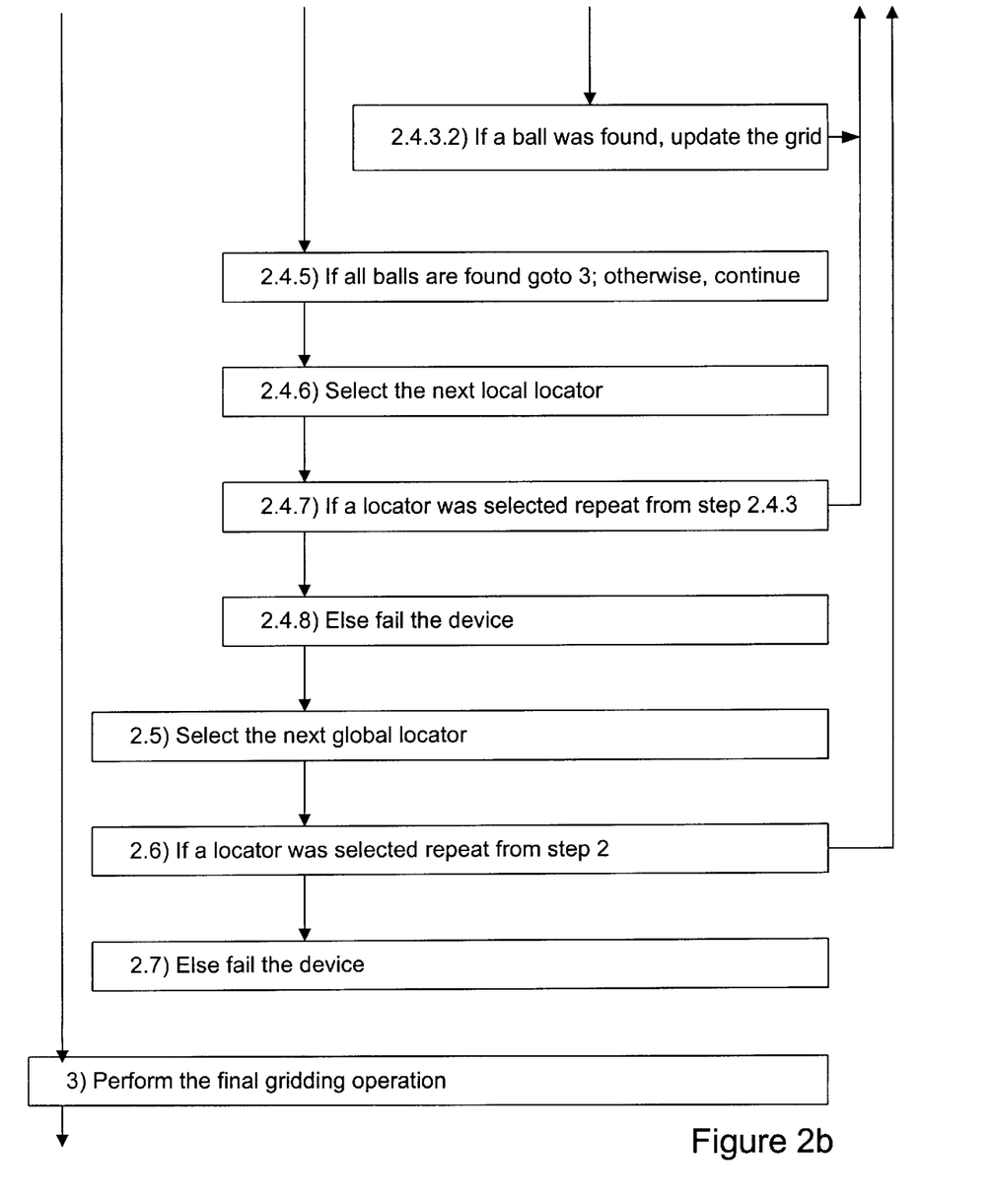
Figure 2C:
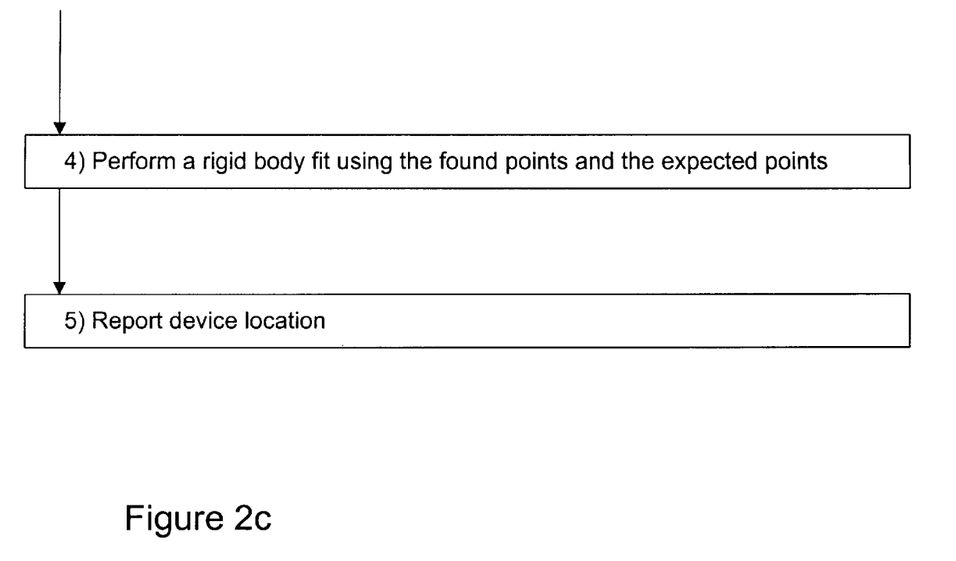

At some later point in time a BGA device that was described to a previous training step is acquired by the system and the inspection is performed. The overall process here is illustrated in FIG. 2 and is spelled out below:

1) Select the first global locator
2) Repeat the following
   2.1) Run the locator on the entire image
   2.2) For each ball found
      2.2.1) Record its location in the locator results
   2.3) If enough balls found (user selectable) go to 3
   2.4) Else if enough balls found to grid
      2.4.1) Perform gridding operation
      2.4.2) Select the first local locator
      2.4.3) Repeat the following for each missing ball
         2.4.3.1) Apply the local locator to the area with the missing ball
         2.4.3.2) If a ball was found, update the grid
         2.4.3.3) Return to step 2.4.3.
      2.4.5) If all the balls are found go to 3
      2.4.6) Select the next local locator
      2.4.7) If a locator was selected repeat from step 2.4.3
      2.4.8) Else fail the device.
   2.5) Select the next global locator
   2.6) If a locator was selected repeat from step 2
   2.7) Else fail the device
3) Perform the final gridding operation
4) Perform a rigid body fit using the found points and the expected points
5) Report device location Training/Inspection Details Construction of a hough locator is performed by using the device description and a calibration which gives the transformation from physical to image space. Using the device description, a hough model of a ball is trained. In addition, the point set data structures are pre-allocated so that at run time this allocation does not need to occur. The point set size is allocated to be equal to the number of balls on the BGA device. Other device specific information is also cached to save time later at run time.

```
long bodyRSize=dd->bodyRSize( ).max( );
long bodyTSize=dd->bodyTSize( ).max( );
```

---

```
// Record the physical space inspection window for the BGA. The
// bounding box is 2x the body size (Note: this should be an input
// parameter).
__phMin.x = -bodyRSize;
__phMin.y = -bodyTSize;
__phMax.x = bodyRSize;
__phMax.y = bodyTSize;
__diameter = dd->ballParams().diameter();
```

-continued

```
const ccBgaElement& elem = dd->elements();
_numBalls += elem.numBallsR() * elem.numBallsT();
if (elem.gridType() == CPS_GRID_CHECKER)
    _numBalls = _numBalls/2 + 1;
else if (elem.gridType() == CPS_GRID_REVERSE_CHECKER)
    _numBalls = _numBalls/2;
else
{
    const ccBgaMissing& missing = elem.missing();
    _numBalls -= missing.numMissingR() * missing.numMissingT();
}
_locatorResults._pointSet = cps_create_pt_set (_numBalls,
                            CPS_CREATE_XYZ);
double pelSize = 1.0/(_pelSizeX + _pelSizeY) * 2.0;
cu_clear ((char *)&_houghParams, sizeof (cbga_params));
_houghParams.diameter = _diameter.nom() * pelSize;
_houghParams.num_bits_ang = CBGA_NUM_BITS_ANG;
_houghParams.run_rej_pct = CBGA_RUN_REJ_PCT;
_houghParams.results = _numBalls;
_houghParams.accept = score;
_houghParams.spread = CBGA_SPREAD;
_houghParams.flags = CBGA_FLAGS;
_houghModel = cbga_train (&_houghParams);
```

Constructing a device inspection is then accomplished by using the previous constructed locator and device description. In one embodiment, the implementation only allows for a single locator to be used. Other embodiments allow for multiple locators of differing types. Here, many of the runtime parameters are precomputed and cached. In particular, the expected location of the balls for an ideal part that is located at the expected location are computed.

```
ct2d_point modelPts;
ccBgaElement& elements = _dd->elements();
ccLocatorResults& locatorResults = _locator->locatorResults();
_rows = elements.numBallsR();
_cols = elements.numBallsT();
for (int i = 0; i < _rows; i++)
for (int j = 0; j < _rows; j++)
{
    if (elements.position (_dd->ballParams(), i, j, modelPts))
        locatorResults.addModelPoint (modelPts.x, modelPts.y);
}
// Allocate the point set information
ccBgaMissing& missing = elements.missing();
_hole.start_row = missing.rBallCoord();
_hole.start_col = missing.tBallCoord();
_hole.rows = missing.numMissingR();
_hole.cols = missing.numMissingT();
_grid = cps_create_grid (_rows, _cols, elements.gridType(),
0, &_hole);
_ptIndex = cps_create_index(locatorResults._pointSet->count,
            locatorResults._pointSet);
```

After these two steps are completed, the device will be in a trained state and ready for inspection.

Device Inspection Details

Further details of the device inspection methodolgy shown in FIG. 2 is provided below:

1) Select the first global locator The first global locator will be the first locator in a list of locators. There are two such lists; the global locators and the local locators.

2) Repeat the following

2.1) Run the locator on the entire image Actually, the locator is run on the inspection window that was computed at training time. This will help improve speed and reduce the chances of find features that are not part of the device.

2.2) For each ball found

2.2.1) Record its location in the locator results. The locator results contains a list of model points that where previous computed during training. Now add the list of found points.

2.3) If enough balls found (user selectable) goto 3 Enough balls will be partially determined by the user. They may say that it is neccessary to find less balls than the device actually contains. In addition, the system must have found enough unique balls to correctly determine the location of the grid. A unique ball would be a corner ball or an edge ball. The test for determining if the ball is a corner ball or an edge ball will be based on distances between the balls on one edge to the opposite edge. If this distance is within ¼ of a ball pitch then these balls will be considered edge or corner balls.

2.4) Else if enough balls are found to perform gridding Here it is not necessary to find the actual grid location. It will be sufficient to have found the grid orientation and its approximate position (within a few rows).

2.4.1) Perform gridding operation Gridding is performed by computing the convex hull of the device. Then, using the convex hull, the angle of the hull computed. Using this angle information, the lattice (grid) can be computed for the balls.

2.4.2) Select the first local locator This is the first locator in the list.

2.4.3) Repeat the following for each missing ball Actually, since the gridding may not have been entirely accurate in location, The selection of a missing ball will be performed as follows:

A) Select all balls that are surrounded by other balls.

B) Select a ball at a potential site. If that ball is not found in the following steps then select a ball at an opposite site. If the ball is still not found then this device has missing balls so contiue at step 2.4.5. See FIG. 4. That Figure illustrates missing ball selection in accord with the illustrated embodiment.

Figure 4:
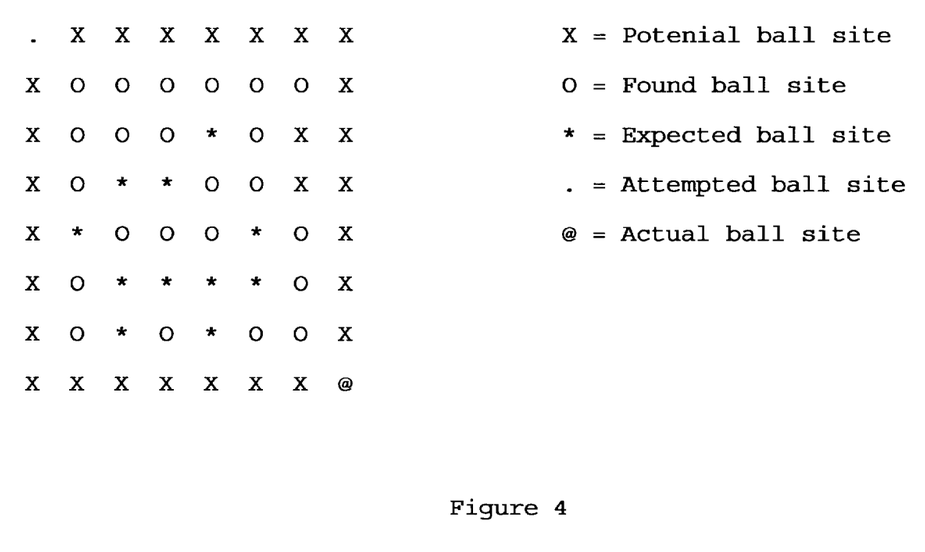
FIG. 4 illustrates missing ball selection in a method according to the invention.

In that Figure, the illustrated BGA has a 7×7 grid of solder bumps. Only a 6×6 grid was found. The * sites will be examined first since these must be balls. The X sites will be examined last since the device could be translated in either direction. The . was the first attempt at locating a ball site. There was no ball present. The @ was the 2nd attempt and a ball was found. At this point, the location of the grid can be determined.

2.4.3.1) Apply the local locator to the area with the missing ball This is actually a potential missing ball site. If the previously computed grid (step 2.4.1) contained enough unique balls then the ball site will be a site that should contain a ball. If enough information was not available then the ball site may be off of the device.

2.4.3.2) If a ball was found, update the grid During the updating process a grid may go from being in an undetermined region to a determinable region.

2.4.3.3) Return to step 2.4.3.

2.4.4) If enough balls are found goto 3

2.4.5) Select the next local locator We allow for multiple locators for cases where the image of the device is such that a single locator methodology does not work. Currently, we anticipate 3 locator technologies; a hough based locator, a blob based locator and a sobel angle image locator. In addition, new locators can be implemented by subclassing from our base locator class.

2.4.6) If a locator was selected repeat from step 2.4.3
2.4.7) Else fail the device.
2.5) Select the next global locator Additional global locators are used for the same reasons that additional local locators are used. Currently there are two proposed global locators. A blob based locator and a hough based locator. Additional locators can be supplied at a later time by either Cognex or the customer.
2.6) If a locator was selected repeat from step 2
2.7) Else fail the device
3) Perform the final gridding operation. This is done to account for all the balls found. This step could actually be combined with the previous step (2.4.3.2) to save time.
4) Perform a rigid body fit using the found points and the expected points This fit is a least-squares 3 paramter fit. The 3 parameters are X translation, Y translation and rotation.
5) Report device location Using the calibration information, the device location in phyical space is computed and returned to the user.

A hough transform tool, as well as other machine vision tools, of the type referred to above for use in conjunction with the illustrated embodiment may be any one of the many such tools commercially available. Preferred such tools are available from the assignee hereof.

As noted above, where the inspection is performed using a general hough transform machine vision tool, that tool can be trained prior to inspection to generate a model of a circle substantially the same size as the expected size of the surface features. That model can be can have, for example, 8-bit or 16-bit resolution depending on a calibration score of the model (i.e., a circle) and an expected image of a surface feature. At the time of inspection, moreover, the general hough transform tool can be applied in a single, exhaustive pass aimed toward locating the circular surface features of the ball grid array surface-mounted device.

A still further understanding of the foregoing methodologies may be attained by reference to U.S. patent application Ser. No. 08/506,295, (Attorney Docket 150448-016), filed Jul. 25, 1995, for IMPROVED MACHINE VISION METHODS AND ARTICLES OF MANUFACTURE FOR DETERMINATION OF CONVEX HULL AND CONVEX HULL ANGLE, the teachings of which are incorporated herein by reference, as well as to the materials provided in the appendix to copending U.S. Provisional Application Ser. No. 60/001,430, filed Jul. 25, 1995, for IMPROVED MACHINE VISION METHODS AND ARTICLES OF MANUFACTURE FOR BALL GRID ARRAY INSPECTION (Attorney Docket No. 150448-006), the teachings of which are also incorporated herein by reference.

Described above are methods for inspecting a BGA device meeting the objects set forth herein. Those methods can be beneficially applied in machine vision applications for the rapid and accurate inspection of BGA devices, without consumption of undue computational resources. From this, the position, orientation and quality of the device as a whole is readily discerned. Such positioning information enables equipment fabricators to precisely position the BGA device on, for example, a printed circuit board. Those methods are amenable to ready application to a range of ball grid arrays devices, such as those with checker board lattices, reverse checker board lattices, and regular lattice with a holes. It will be appreciated that the embodiments described herein are not intended to be limiting, and that other embodiments incorporating additions, deletions and other modifications within the ken of one of ordinary skill in the art are in the scope of the invention.

In view of the foregoing, what I claim is:

1. A method of inspecting an image to locate a ball grid array surface-mounted device that is characterized by an array of similar surface features the method comprising:
   A. inspecting the image to find said surface features and to determine their observed locations,
   B. comparing expected locations of the surface features with the observed locations to identify any surface features that are apparently missing, wherein the comparing step comprises
      determining, from the observed locations of the surface features found in the inspecting step, a convex hull and its angle,
      determining, from the convex hull and its angle, a grid of expected locations of the surface features,
   C. reinspecting the image in a vicinity of an apparently missing surface feature to find that apparently missing surface feature and to determine its observed location, and
   D. determining, from the observed locations of the surface features found in the inspecting and reinspecting steps, any of a position and an angle of the ball grid array surface mounted device.

2. A method according to claim 1, wherein the grid comprises any of a regular lattice, a checker board lattice, a reverse checker board lattice, a regular lattice with a hole, and a custom lattice.

3. A method according to claim 1, wherein the determining step comprises identifying the position and angle of the ball grid array surface-mounted device by performing a rigid body fit of the observed locations of surface features to the grid of expected locations.

4. A method of inspecting an image to locate a ball grid array surface-mounted device that is characterized by an array of similar surface features, the method comprising:
   A. inspecting the image to find said surface features and to determine their observed locations,
   B. comparing expected locations of the surface features with the observed locations to identify any surface features that are apparently missing, the comparing step including
      i. determining, from the observed locations of the surface features found in the inspecting step, a convex hull and its angle,
      ii. determining, from the convex hull and its angle, a grid of expected locations of the surface features,
      iii. identifying vertices of the grid of expected locations,
      iv. finding a vertex closest to the observed location of each found surface feature and assigning that feature to that vertex, and
      v. generating a score based on a number of found surface features assigned to each vertex and the distance between that vertex and its assigned surface features,
   reinspecting the image in a vicinity of an apparently missing surface feature to find that apparently missing surface feature and to determine its observed location, and
   determining, from the observed locations of the surface features found in the inspecting and reinspecting steps, any of a position and an angle of the ball grid array surface mounted device.

5. An article of manufacture comprising a computer usable medium embodying program code for causing a digital data processor to carry out a method of inspecting an image to locate a ball grid array surface-mounted device that is characterized by an array of similar surface features, the method comprising:

A. inspecting the image to find those surface features and to determine their observed locations, B. comparing expected locations of the surface features with the observed locations to identify any surface features that are apparently missing, wherein the comparing step comprises determining, from the observed locations of the surface features found in the inspecting step, a convex hull and its angle, determining, from the convex hull and its angle, a grid of expected locations of the surface features, C. reinspecting the image in a vicinity of an apparently missing surface feature to find that surface feature and to determine its observed location, and D. determining, from the observed locations of the surface features found in the inspecting and reinspecting steps, any of a position and an angle of the ball grid array surface-mounted device.

* * * * *